United States Patent
Soppera et al.

(10) Patent No.: US 11,548,215 B2
(45) Date of Patent: Jan. 10, 2023

(54) METHOD OF PRODUCING AN OPTICAL DEVICE AND A CORRESPONDING SYSTEM

(71) Applicants: NIKON CORPORATION, Tokyo (JP); Essilor International, Charenton-le-Pont (FR); CENTRE NATIONAL DE LA RECHERCHE SCIENTIFIQUE, Paris (FR); UNIVERSITE DE HAUTE-ALSACE (UHA), Mulhouse (FR)

(72) Inventors: Olivier Soppera, Mulhouse (FR); Manuel Theodet, Tokyo (JP)

(73) Assignees: NIKON CORPORATION, Tokyo (JP); ESSILOR INTERNATIONAL, Charenton-le-Pont (FR); CENTRE NATIONAL DE LA RECHERCHE SCIENTIFIQUE, Paris (FR); UNIVERSITE DE HAUTE-ALSACE (UHA), Mulhouse (FR)

( * ) Notice: Subject to any disclaimer, the term of this patent is extended or adjusted under 35 U.S.C. 154(b) by 165 days.

(21) Appl. No.: 16/625,267

(22) PCT Filed: Jun. 30, 2017

(86) PCT No.: PCT/IB2017/001012
§ 371 (c)(1),
(2) Date: Dec. 20, 2019

(87) PCT Pub. No.: WO2019/002905
PCT Pub. Date: Jan. 3, 2019

(65) Prior Publication Data
US 2020/0215747 A1    Jul. 9, 2020

(51) Int. Cl.
*B29C 64/135*    (2017.01)
*B33Y 10/00*    (2015.01)
(Continued)

(52) U.S. Cl.
CPC .............. *B29C 64/135* (2017.08); *A61F 2/16* (2013.01); *B29C 64/264* (2017.08); *B33Y 10/00* (2014.12);
(Continued)

(58) Field of Classification Search
CPC ..... B29C 64/135; B29C 64/264; B33Y 10/00; B33Y 80/00; B29K 2033/08
See application file for complete search history.

(56) References Cited

U.S. PATENT DOCUMENTS 5,597,519 A    1/1997    Martin et al.
2001/0047217 A1    11/2001    Buazza et al.
(Continued)

FOREIGN PATENT DOCUMENTS

EP    0686484 A2    6/1995
EP    1284426 A2    2/2003
(Continued)

OTHER PUBLICATIONS

English language machine translation of JP-4767836. (Year: 2011).*
(Continued)

*Primary Examiner* — Larry W Thrower
(74) *Attorney, Agent, or Firm* — Nixon & Vanderhye

(57) ABSTRACT

A method of producing an optical device from a volume of a curable composition, includes the following steps: —polymerizing a first portion of the volume by irradiating an external surface of the volume with a light irradiation, thereby increasing a transmittance of the first portion for the light irradiation; —polymerizing a second portion of the volume by irradiating the second portion with the light irradiation through the external surface and the polymerized first portion, wherein the light irradiation has a light intensity varying over the external surface between a first light intensity and a second light intensity distinct from the (Continued)

second light intensity. A corresponding system is also described.

18 Claims, 2 Drawing Sheets

(51) Int. Cl.
| | |
|---|---|
| *B33Y 30/00* | (2015.01) |
| *B33Y 70/00* | (2020.01) |
| *B33Y 80/00* | (2015.01) |
| *B29C 64/264* | (2017.01) |
| *A61F 2/16* | (2006.01) |
| *G02B 1/04* | (2006.01) |
| *B29K 33/00* | (2006.01) |
| *B29L 11/00* | (2006.01) |

(52) U.S. Cl.
CPC ............ *B33Y 30/00* (2014.12); *B33Y 70/00* (2014.12); *B33Y 80/00* (2014.12); *G02B 1/041* (2013.01); *A61F 2240/001* (2013.01); *B29K 2033/08* (2013.01); *B29L 2011/0008* (2013.01); *B29L 2011/0016* (2013.01); *B29L 2011/0041* (2013.01)

(56) References Cited

U.S. PATENT DOCUMENTS

| | | | |
|---|---|---|---|
| 2003/0031414 A1 | 2/2003 | Inui et al. | |
| 2004/0080938 A1* | 4/2004 | Holman | G02F 1/133605 362/231 |
| 2005/0148682 A1* | 7/2005 | Hu | C08F 283/12 523/106 |
| 2006/0050399 A1* | 3/2006 | Nakagawa | G02B 3/02 359/642 |
| 2016/0046075 A1 | 2/2016 | Desimone et al. | |
| 2016/0136889 A1 | 5/2016 | Rolland et al. | |
| 2016/0137838 A1 | 5/2016 | Rolland et al. | |
| 2016/0137839 A1 | 5/2016 | Rolland et al. | |
| 2016/0160077 A1 | 6/2016 | Rolland et al. | |
| 2017/0371091 A1* | 12/2017 | Seydel | G02B 6/29337 |

FOREIGN PATENT DOCUMENTS

| | | |
|---|---|---|
| JP | H01-198312 A | 8/1989 |
| JP | H08-52818 A | 2/1996 |
| JP | 2003-057476 A | 2/2003 |
| JP | 2006-076026 A | 3/2006 |
| JP | 2010-264602 A | 11/2010 |
| JP | 4767836 * | 9/2011 |
| JP | 2013-125059 A | 6/2013 |
| WO | 02/087861 A2 | 11/2002 |
| WO | 03/074149 A1 | 9/2003 |
| WO | 2015/195909 A1 | 12/2015 |
| WO | 2015/195920 A1 | 12/2015 |
| WO | 2015/195924 A1 | 12/2015 |
| WO | 2015/200173 A1 | 12/2015 |
| WO | 2016/007495 A1 | 1/2016 |
| WO | 2016/025599 A1 | 2/2016 |

OTHER PUBLICATIONS

International Search Report, dated Mar. 1, 2018, from corresponding PCT application No. PCT/IB2017/001012.
Cui, Y. et al., "In situ fabrication of polyacrylate/ nanozirconia hybrid material via frontal photopolymerization," Colloid Polym Sci (2008) 286:97-106.
Cui, Y. et al., "Monitoring frontal photopolymerization by electroresistance," European Polymer Journal 43 (2007) 3912-3922.
Cui, Y. et al., "Unique morphology and properties study of polyacrylate obtained via frontal photopolymerization," Polymer 48 (2007) 5994-6001.
Hayki, N. et al., "Kinetic Study of Photoinitiated Frontal Polymerization. Influence of UV Light Intensity Variations on the Conversion Profiles," Macromolecules 2010, 43, 177-184.
Hennessy, M. et al., "Controlling frontal photopolymerization with optical attenuation and mass diffusion," Physical Review E 91, 062402 (2015).
Hennessy, M. et al., "Role of heat generation and thermal diffusion during frontal photopolymerization," Physical Review E 92, 022403 (2015).
Ivanov, V. and Decker, C., "Kinetic study of photoinitiated frontal polymerization," Polym Int 50:113-118 (2001).
Kostarev, K. et al., "Formation of Inhomogeneities in Polyacrylamide Gel in the Course of Frontal Polymerization," Polymer Science, Ser. A, 2008, vol. 50., No. 6, pp. 710-715.
Muller, G. et al., "Modeling of Photobleaching for the Photoinitiation of Thick Polymerization Systems," Journal of Polymer Science: Part A: Polymer Chemistry, vol. 40, 793-808 (2002).
Tao, Y. et al., "Study of spatial-temporal kinetics of photo-initiated frontal polymerization in stacked reaction cells," Polymer Int 55:418-425 (2006).
Terranoes, G. and Pearlstein, A. et al., "Effects of Optical Attenuation and Consumption of a Photobleaching Initiator on Local Initiation Rates in Photopolymerizations," Macromolecules 2001, 34, 3195-3204.
Turturro, M. and Papavasiliou, G., "Generation of Mechanical and Biofunctional Gradients in PEG Diacrylate Hydrogels by Perfusion-Based Frontal Photopolymerization," Journal of Biomaterials Science, Polymer Edition, 23:7, 917-939, 2012.
Vitale, A. et al., "A Unified Approach for Patterning via Frontal Photopolymerization," Adv. Mater. 2015, 27, 6118-6124.
Vitale, A., et al., "Interfacial Profile and Propagation of Frontal Photopolymerization Waves," Macromolecules, 2015, 48, 198-205.
Warren, J. et al., "Solution of a field theory model of frontal photopolymerization," Physical Review E 72, 021801 (2005).

* cited by examiner

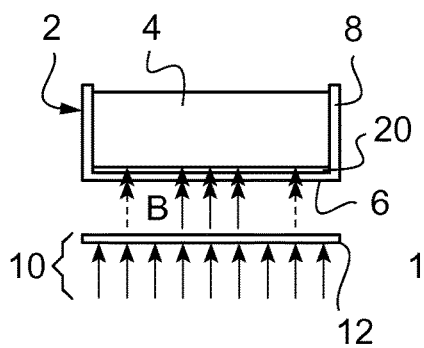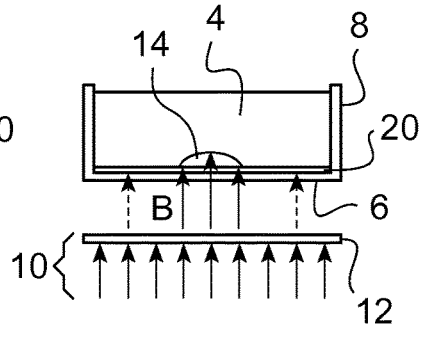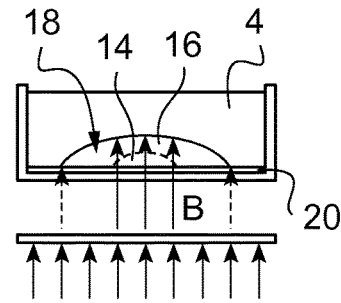
Fig.1    Fig.2    Fig.3
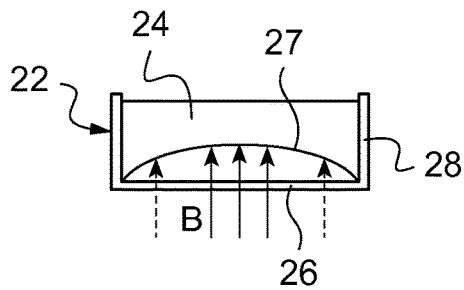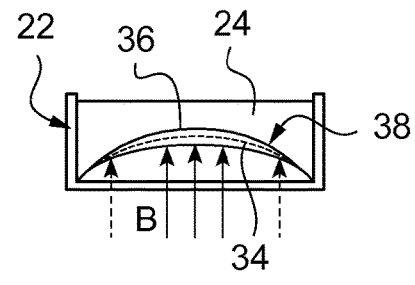
Fig.4    Fig.5
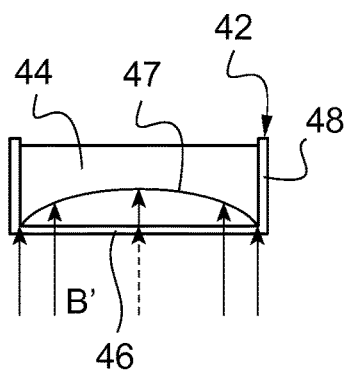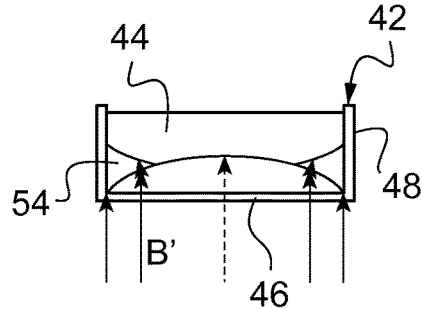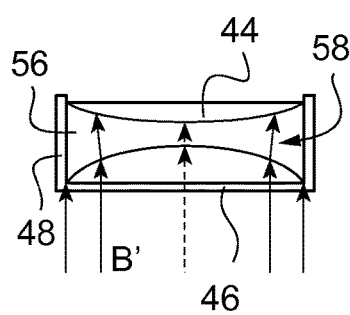
Fig.6    Fig.7    Fig.8

METHOD OF PRODUCING AN OPTICAL DEVICE AND A CORRESPONDING SYSTEM

TECHNICAL FIELD OF THE INVENTION

The invention relates to the production of optical devices, such as optical lenses.

More precisely the invention relates to a method of producing an optical device and to a corresponding system.

BACKGROUND INFORMATION AND PRIOR ART

It has been sought to produce optical devices such as optical lenses using 3D printing technologies, which could offer significant advantages over conventional methods.

Some 3D printing technologies may however not be well suited to produce optical devices, owing in particular to the internal transparency and accurate shape at interfaces necessary for this kind of products.

SUMMARY OF THE INVENTION

In this context, the invention provides a method of producing an optical device from a volume of a curable composition, comprising the following steps:
  polymerizing a first portion of said volume by irradiating an external surface of said volume with a light irradiation, thereby increasing a transmittance of said first portion for said light irradiation;
  polymerizing a second portion of said volume by irradiating said second portion with said light irradiation through said external surface and the polymerized first portion,
wherein said light irradiation has a light intensity varying over said external surface between a first light intensity and a second light intensity distinct from said second light intensity.

Polymerization is thus performed continuously from portion to portion of the curable composition, which makes it possible to obtain an homogeneous polymerized material, having therefore a good transparency.

In addition, thanks to the use of a light irradiation having a specific distribution, the shape of the optical device obtained can be controlled in accordance with optical requirements.

The invention also provides the following optional (and thus non-limiting) aspects:
  said power is varying over time for at least one point of said external surface;
  said light irradiation is in the ultraviolet range;
  said light irradiation is in the visible range;
  said curable composition includes a photo-initiator sensitive to the light irradiation and having photobleaching properties, meaning that it becomes transparent to the light irradiation wavelength after having reacted with the light irradiation;
  said photo-initiator is a Bis Acyl Phosphine Oxide (BAPO) or a 2, 4, 6-trimethylbenzoylphenyl phosphinate (Irgacure TPO);
  said curable composition contains an acrylate;
  the method comprises a step of degassing the curable composition prior to polymerizing said first portion;
  said optical device is an optical lens;
  in particular, the optical device is an ophthalmic lens;
  said curable composition is in a container with a bottom part;
  the optical device is formed by polymerization starting from the bottom part;
  said light irradiation is transmitted through said bottom part;
  said bottom part has a curved shape, spherical or aspheric, facing said volume, whereby the bottom part of the produced optical device has a corresponding curved shape;
  said bottom part has a convex shape facing said volume, whereby the bottom part of the produced optical device has a concave shape;
  said varying light intensity presents a maximum value in the centre of said external surface, usable for example to form a positive optical lens;
  said varying light intensity presents a maximum value at the periphery of said external surface, usable for example to form a negative optical lens;
  said varying light intensity presents a maximum value at the periphery of said external surface, along a first axis, and presents a lower value along an axis perpendicular to said first axis, usable for example to form a toric optical lens;
  said varying light intensity presents a maximum value in a decentered position within said external surface, usable for example to form an optical lens bearing an addition;
  said varying light intensity presents a combination of the above patterns;
  said light irradiation is produced by an emitter comprising a spatial light modulator.

The invention also provides a system for producing an optical device, comprising:
  a container containing a volume of a curable composition; and
  an emitter of a light irradiation arranged to irradiate an external surface of said volume through the container, thereby polymerizing a first portion of said volume and increasing a transmittance of said first portion for said electromagnetic radiation, such that a second portion of said volume is polymerized by irradiating said second portion with said electromagnetic radiation through said external surface and the polymerized first portion,
wherein said light irradiation has a light intensity varying over said external surface between a first light intensity and a second light intensity distinct from said second light intensity.

This system may also include a control module for controlling said emitter to produce said varying light intensity.

Optional features presented above in connection with the proposed method may also apply to this system.

The present invention can be used for all kinds of optical devices and elements, such as optical lenses and devices or ophthalmic elements and devices. Non-limiting examples of ophthalmic elements include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors such as found in spectacles, glasses, goggles and helmets.

DETAILED DESCRIPTION OF EXAMPLE(S)

Illustrative embodiments of the present invention are described in detail below with reference to the attached drawing Figures, wherein FIG. 1 shows a first example of a system for producing an optical device in an initial step;

FIG. 2 shows the system of FIG. 1 in an intermediary step;

FIG. 3 shows the system of FIG. 1 in a final step;

FIG. 4 shows a second example of a system for producing an optical device in an initial step;

FIG. 5 shows the system of FIG. 4 in a final step;

FIG. 6 shows a third example of a system for producing an optical device in an initial step;

FIG. 7 shows the system of FIG. 6 in an intermediary step;

FIG. 8 shows the system of FIG. 6 in a final step;

FIGS. 1 to 3 show respectively three distinct steps of a method for producing an optical device using an exemplary system for producing an optical device.

Figure 9:
FIGS. 9 to 11 show distinct light distributions successively applied to a container containing a curable composition as in the system above.

This system comprises a container 2 containing a volume of a curable composition 4.

The container 2 comprises a bottom part 6 and lateral walls 8 making it possible to hold the volume of curable composition 4.

The system further comprises a light emitter 10 emitting a light beam B towards the container 2, precisely towards the bottom part 6.

The type of light used may be ultraviolet light, or visible light, for instance.

The light emitter 10 comprises for instance a light generator (not represented) generating collimated light rays and a spatial light modulator 12 applied to the collimated light rays such that the light beam B has a light intensity varying over the beam B itself (in a manner controllable thanks to the spatial light modulator 12). The spatial light modulator 12 is for instance adapted to control the distribution of light in the light beam under control by a control module. The spatial distribution (as well as possibly its temporal evolution) can thus be configured by a user programming said control module.

In the present example, as schematically shown in FIGS. 1 to 3, light intensity is higher in the centre of the beam B than at the periphery of the beam B.

At least the bottom part 6 of the container 2 (and possibly the whole container 2) is transparent to light emitted by the light emitter 10 (or, at least, translucent for light emitted by the light emitter 10). In this purpose, the container may be made of quartz, for instance.

As depicted in FIG. 1, light emitted by the light emitter 10 thus irradiates an external surface of the volume of the curable composition 4 (here: the external surface facing the bottom part 6), here through the container 2 (precisely through the bottom part 6 of the container 2). As the light beam B is not homogeneous (here: thanks to the use of the spatial light modulator 12), this light irradiation has a light intensity varying over the external surface between a first light intensity and a second light intensity distinct from said second light intensity.

The curable composition 4 comprises for instance a resin (made of a monomer such as an acrylate, for instance Dipentaerythritol penta-/hexa-acrylate or PETIA) and a photo-initiator, such as Bis Acyl Phosphine Oxide (BAPO).

According to a possible variation, the curable composition may include:

2.2 Bis(4-(Acryloxy Diethoxy)Phenyl)Propane(EO4 mol), or A-BPE-4, to provide the main optical and mechanical properties (for instance between 25 wt % and 95 wt %);

Isobornyl Acrylate, or A-IB, to adjust the optical and mechanical properties (for instance between 5 wt % and 75 wt %);

3-methyl-2-buten-1-ol to prevent yellowing (for instance between 1 wt % and 3 wt %, here 2 wt %);

2, 4, 6-trimethylbenzoylphenyl phosphinate, or Irgacure TPO, as a photo-bleachable photo-initiator (for instance between 1 wt % and 5 wt %, preferably between 2 wt % and 3 wt %).

At least part of the curable composition 4 (here the photo-initiator) has photo-bleaching properties, i.e. becomes transparent to the light it receives after having reacted due to this light.

As the beam of light is not homogeneous, polymerization of the curable composition 4 develops first in regions where light intensity is high, here in the centre of the beam B (and thus in the centre of the bottom part 6), leading to the formation of a first polymerized portion 14, as shown in FIG. 2.

Due to the photo-bleaching properties of the curable composition 4, the first polymerized portion 14 becomes transparent to light received from the light emitter 10: the transmittance of the first portion 14 for the light received from the light emitter 10 increases while the first portion 14 polymerizes.

Thus, light entering via the bottom part 6 of the container 2 in the region of the first polymerized portion 14 then transmits across the first polymerized portion 14 (as schematically shown in FIG. 2) and reaches a second portion 16 of the volume of the curable composition 4, thereby leading to polymerization of this second portion 16 (as shown in FIG. 3).

As already noted, owing to variations of light intensity across the light beam B, polymerization develops more rapidly in regions where light intensity is high and the thickness of polymerized material is therefore variable over the bottom part 6 of the container 2.

In the present case, as light intensity is high in the centre of the light beam and decreases towards its periphery, the polymerized material has a convex shape, as visible in FIGS. 2 and 3.

In its final state shown in FIG. 3, the polymerized material obtained (including the first portion 14 and the second portion 16) forms an optical lens 18. This optical lens 18 can be removed from the container 2 and possibly subjected to post-treatment, such as a final curing (post-polymerization), to obtain a good surface state, in particular.

In this respect, a dedicated anti-adhesive (transparent) layer 20 may be interposed between the bottom part 6 of the container 2 and the curable composition 4 to ease removal of the optical lens 18 from the container 2.

In the example just described referring to FIGS. 1 to 3, the bottom part 6 of the container 2 has a planar surface facing the curable composition 4 such that the optical lens 18 obtained is a plano-convex optical lens.

The bottom part 6 of the container 2, which defines one of the faces of the optical lens, can however have a non planar shape, as exemplified below.

FIGS. 4 and 5 show another embodiment of a system for producing an optical device.

As in the previous embodiment, a container 22 holds a volume of a curable composition 24. Examples of curable composition given above also apply in the present embodiment. The curable composition (or at least non-transparent compounds of the curable composition) has photo-bleaching properties, as explained above.

The container 22 has a bottom part 26 and lateral walls 28. In the present embodiment, the surface 27 of the bottom part 26 facing the volume of curable composition 24 (here in contact with the volume of curable composition 24), i.e. the top surface of the bottom part 26, has a convex shape, as visible in FIGS. 4 and 5.

A non-homogeneous light beam B is applied to the external surface of the bottom part 26. This light beam B is here of the same type as the light beam used in the embodiment of FIGS. 1 to 3 and can thus be generated in a similar manner. Light intensity is thus higher in the centre of the light beam B than at its periphery.

The bottom part 26 (at least) of the container 22 is transparent to light used for the light beam B such that the light beam B irradiates an external surface of the volume of the curable composition 24 (i.e. here the surface in contact with the top surface 27 of the bottom part 26 of the container 22).

In the initial state shown in FIG. 4, no portion of the volume of the curable composition 24 has yet polymerized and irradiation by the light beam B through the bottom part 26 thus leads to polymerizing regions of the volume of the curable composition 24 in the vicinity of the bottom part 26, corresponding to a first portion 24 of this volume (schematically shown in FIG. 5).

As the light beam is non-homogenous (light intensity being here higher in the centre), polymerization is more active in some regions (here the centre) than in others (here the periphery) and the first (polymerized) portion 34 has consequently a thickness varying over the bottom part 26 of the container 22 (here: a thickness increasing towards its centre).

Thus, at a time intermediate between the initial and final steps, the first portion 34 has polymerized and the transmittance of the first portion 34 has increased due to the photo-bleaching properties of the curable composition.

The light beam B irradiating the bottom part 26 of the container 22 and transmitted across the bottom part 26 thus propagates through the polymerized first portion 34 and thereby reaches a second portion 36 of the volume of the curable composition 24, which consequently polymerizes in turn.

As for the first portion 34, the polymerization of the second portion 36 is faster in regions where light intensity is higher and the second (polymerized) portion 26 thus has a thickness varying over the bottom part 26 of the container 22 (here: a thickness increasing towards its centre).

As shown in FIG. 5 (corresponding to the final step of the method for producing an optical device, here an optical lens 38), the polymerized material extends on the convex top surface 27 of the bottom part 26 and has a thickness increasing towards its centre: the polymerized material can thus form a concavo-convex lens 38 which can be used for instance as an optical lens.

As mentioned for the previous embodiment, a final treatment (post-polymerization step) may be applied to the optical lens 38 after removal from the container 22, by subjecting the optical lens 38 removed from the container 22 to light, for instance of the same type as the light beam B mentioned above. This post-polymerization steps makes it possible to obtain a good surface state of the optical lens 38, in particular FIGS. 6 to 8 shows yet another example of a system for producing an optical device.

In an initial step shown in FIG. 6, a volume of a curable composition 44 is put in a container 42.

The container 42 is here identical to the container 22 of FIGS. 4 and 5: the container 42 has a bottom part 46 and lateral walls 48 and the surface 47 of the bottom part 46 facing the volume of curable composition 44 (here in contact with the volume of curable composition 44), i.e. the top surface of the bottom part 46, has a convex shape.

The curable composition (or at least non-transparent components of the curable composition) has photo-bleaching properties, as explained above.

A non-homogeneous light beam B' is applied to the external surface of the bottom part 26. This light beam B' has a higher light intensity at its periphery than at its centre. Said differently, the light intensity in the light beam B' decreases towards the centre of the light beam B'. Such a light beam B' can be obtained using a spatial light modulator, as described above referring to FIGS. 1 to 3.

The bottom part 46 (at least) of the container 42 is transparent to light used for the light beam B' such that the light beam B' irradiates an external surface of the volume of the curable composition 44 (i.e. here the surface in contact with the top surface 47 of the bottom part 46 of the container 42).

In the initial state shown in FIG. 6, as no portion of the volume of the curable composition 44 has yet polymerized, irradiation by the light beam B' through the bottom part 46 thus leads to polymerizing regions of the volume of the curable composition 44 in the vicinity of the bottom part 46. However, as the light beam is non-homogenous (light intensity being here higher at the periphery of the light beam B'), polymerization begins in particular at the periphery of the volume of curable composition 44, in first portions 54 schematically shown in FIG. 7.

As a consequence, at an intermediary step shown in FIG. 7, these first portions 54 have polymerized and the transmittance of these first portions 54 has increased due to the photo-bleaching properties of the curable composition.

The light beam B' irradiating the bottom part 46 of the container 42 and transmitted across the bottom part 46 thus propagates through the polymerized first portion 54, as schematically shown in FIG. 7, and thereby reaches second portions 56 of the volume of the curable composition 44, which consequently polymerizes in turn.

As the light beam B' is not homogeneous, this process is more effective in regions where the light intensity is high, leading to a larger thickness in these (here peripheral) regions.

Consequently, in the final step shown in FIG. 8, the polymerized material extends on the convex top surface 47 of the bottom part 46 with a thickness decreasing towards its centre: the polymerized material can thus form a double concave lens 58 which can be used for instance as an optical lens.

As mentioned for previous embodiments, a final treatment (post-polymerization step) may be applied to the optical lens 58 after removal from the container 42. This post-polymerization step makes it possible to obtain a good surface state of the optical lens 58, in particular.

In the examples just described, the light beam B, B' irradiating the volume of the curable composition is non homogeneous spatially, but has constant characteristics over time. In other embodiments, light distribution in the light beam could evolve over time, as now explained.

Example A

Figure 10:
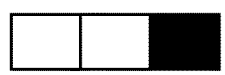
Figure 11:
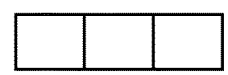
Figure 12:
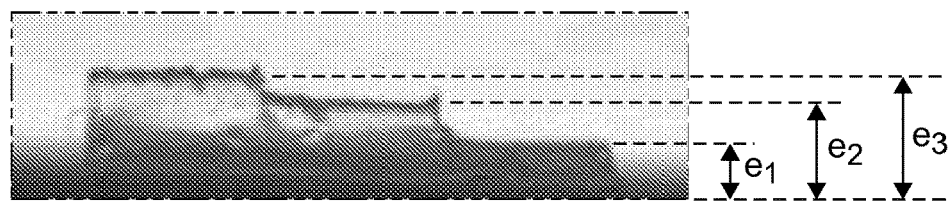
FIG. 12 shows a piece of polymerized material obtained by applying these light distributions.

A piece of polymerized material with variable thickness as shown in FIG. 12 was obtained by subjecting a curable composition (having a volume of 38 cm³) placed in a container (identical to the container 2 of FIG. 1) to a light beam having successively the three distinct light distributions shown respectively in FIGS. 9 to 11.

The curable composition used comprises PETIA (Dipentaerythritol penta-/hexa-acrylate), as a monomer, and 1% (in weight) of Bis Acyl Phosphine Oxide (BAPO), as a photo-initiator. Light used is visible light.

In FIGS. 9 to 11, white areas represent parts of the light beam with high intensity (for instance between 10 W·m$^{-2}$ and 100 W·m$^{-2}$, here about 40 W·m$^{-2}$), while black areas represent parts of the light beam with low (or no) light intensity.

Prior to being subjected to the light beam, the curable composition is degassed (here for an hour at 0.09 MPa) to removed dissolved $O_2$.

The light distribution shown in FIG. 9 is applied for 5 s.
Then, the light distribution shown in FIG. 10 is applied for 5 s.
Then, the light distribution shown in FIG. 11 is applied for 10 s.

The piece of polymerized material obtained is shown in FIG. 12.

Three distinct thicknesses are clearly visible:
$\theta_1$=1.5 mm (obtained by the 10s-long irradiation of the right-hand part of the beam on FIG. 11);
$\theta_2$=2.6 mm (obtained by the 15s-long irradiation of the central part of the beam);
$\theta_3$=3.35 mm (obtained by the 20s-long irradiation of the left-hand part of the beam).

Example B

Figure 13:
FIGS. 13 to 15 show lenses obtained using the process described above with reference to FIGS. 1 to 3 for distinct operating conditions.
Figure 14:
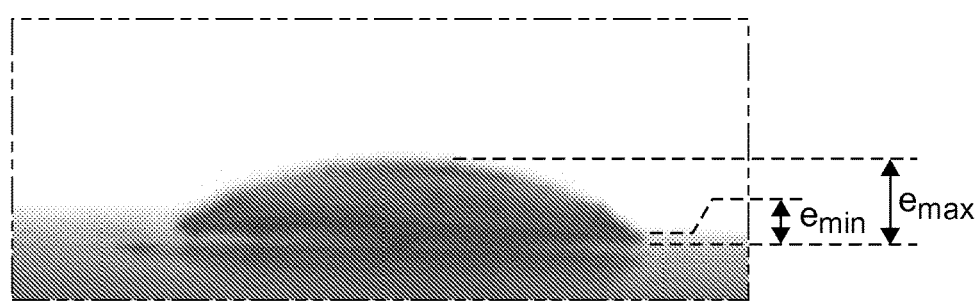
Figure 15:
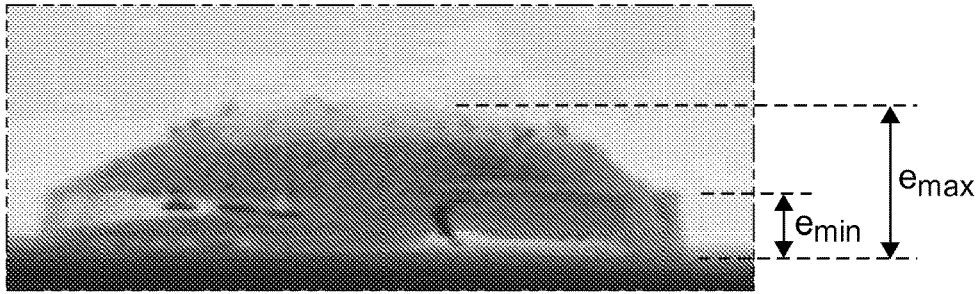

FIGS. 13 to 15 show plano-convex lenses obtained using the process described above with reference to FIGS. 1 to 3 for distinct operating conditions, respectively.

The curable composition used comprises PETIA (Dipentaerythritol penta-/hexa-acrylate), as a monomer, and 1% (in weight) of Bis Acyl Phosphine Oxide (BAPO), as a photo-initiator. Light used is visible light.

The light distribution of the light beam has rotational symmetry around the centre of the light beam (where light intensity is maximum, in the present example).

Operating conditions and characteristics of the obtained lenses (maximum thickness $e_{max}$ and minimum thickness $e_{min}$) are given in the table below.

|  | FIG. 13 | FIG. 14 | FIG. 15 |
| --- | --- | --- | --- |
| Light intensity at centre | 10 W·m$^{-2}$ | 10 W·m$^{-2}$ | 10 W·m$^{-2}$ |
| Light intensity at periphery | 3 W·m$^{-2}$ | 3 W·m$^{-2}$ | 3 W·m$^{-2}$ |
| Degassing | no | yes: hard | yes: mild |
| $e_{max}$ | 3.36 mm | 2.26 mm | 4.77 mm |
| $e_{min}$ | 1.63 mm | 0.62 mm | 2.11 mm |

The above experiments correspond only to exemplary embodiments of the invention and the values mentioned therein should not therefore be construed as limitative.

The invention claimed is:

1. A method of producing an optical device from a volume of a curable composition, comprising the following steps:
  polymerizing a first portion of said volume by irradiating an external surface of said volume with a light irradiation, thereby increasing a transmittance of said first portion for said light irradiation;
  polymerizing a second portion of said volume by irradiating said second portion with said light irradiation through said external surface and the polymerized first portion,
  wherein said light irradiation has a light intensity varying over said external surface between a first light intensity and a second light intensity distinct from said first light intensity, and
  wherein the step of polymerizing the first portion and the step of polymerizing the second portion are performed continuously from portion to portion of the curable composition to obtain a homogeneous transparent polymerized material.

2. The method of claim 1, wherein said light intensity is varying over time for at least one point of said external surface.

3. The method of claim 1, wherein said light irradiation is in the ultraviolet range.

4. The method of claim 1, wherein said light irradiation is in the visible range.

5. The method of claim 1, wherein said curable composition includes a photo-initiator sensitive to the light irradiation and having photobleaching properties.

6. The method of claim 5, wherein said photo-initiator is a Bis Acyl Phosphine Oxide.

7. The method of claim 1, wherein said curable composition contains an acrylate.

8. The method of claim 1, comprising a step of degassing the curable composition prior to polymerizing said first portion.

9. The method of claim 1, wherein said optical device is an optical lens.

10. The method of claim 1, wherein said curable composition is in a container with a bottom part; wherein the optical device is formed by polymerization starting from the bottom part; and wherein said light irradiation is transmitted through said bottom part.

11. The method of claim 10, wherein said bottom part has a convex shape facing said volume, whereby the produced optical device has a concave shape.

12. The method of claim 1, wherein light intensity in a center of said external surface is greater than light intensity at a periphery of said external surface.

13. The method of claim 1, wherein light intensity at a periphery of said external surface is greater than light intensity at a center of said external surface.

14. The method of claim 1, wherein said light irradiation is produced by an emitter comprising a spatial light modulator.

15. The method of claim 2, wherein said light irradiation is in the ultraviolet range.

16. The method of claim 2, wherein said light irradiation is in the visible range.

17. The method of claim 2, wherein said curable composition includes a photo-initiator sensitive to the light irradiation and having photobleaching properties.

18. The method of claim 3, wherein said curable composition includes a photo-initiator sensitive to the light irradiation and having photobleaching properties.

* * * * *